(12) United States Patent
Atadja

(10) Patent No.: US 8,883,842 B2
(45) Date of Patent: Nov. 11, 2014

(54) USE OF HDAC INHIBITORS FOR THE TREATMENT OF MYELOMA

(75) Inventor: Peter W Atadja, Acton, MA (US)

(73) Assignee: Novartis AG, Basel (CH)

( * ) Notice: Subject to any disclaimer, the term of this patent is extended or adjusted under 35 U.S.C. 154(b) by 682 days.

(21) Appl. No.: 12/717,373

(22) Filed: Mar. 4, 2010

(65) Prior Publication Data
US 2010/0160257 A1 Jun. 24, 2010

Related U.S. Application Data

(63) Continuation of application No. 11/996,323, filed as application No. PCT/US2006/029801 on Aug. 1, 2006, now abandoned.

(60) Provisional application No. 60/705,226, filed on Aug. 3, 2005.

(51) Int. Cl.
*A61K 31/165* (2006.01)
*A61K 31/4045* (2006.01)
*A61K 31/4965* (2006.01)

(52) U.S. Cl.
CPC ............ *A61K 31/165* (2013.01); *A61K 31/4965* (2013.01); *A61K 31/4045* (2013.01)
USPC ..................... 514/415; 514/255.06

(58) Field of Classification Search
CPC .......... A61K 31/165; A61K 31/4965
See application file for complete search history.

(56) References Cited

U.S. PATENT DOCUMENTS

| | | | |
|---|---|---|---|
| 2004/0024067 A1* | 2/2004 | Remiszewski et al. | 514/575 |
| 2004/0132825 A1 | 7/2004 | Bacopoulos et al. | |
| 2004/0167134 A1 | 8/2004 | Bruns et al. | |
| 2007/0123580 A1 | 5/2007 | Atadja et al. | |

FOREIGN PATENT DOCUMENTS

| | | |
|---|---|---|
| WO | 02/22577 | 3/2002 |
| WO | 03/048774 | 6/2003 |
| WO | 2004/096224 | 11/2004 |
| WO | 2004/103358 A2 * | 12/2004 |
| WO | 2005/023179 | 3/2005 |
| WO | WO2006/102557 | 9/2006 |

OTHER PUBLICATIONS

Registry No. 179324-69-7 (Entered STN Aug. 9, 1996; Accessed Aug. 7, 2012).*
Catley et al., "NVP-LAQ824 is a potent novel histone deacetylase inhibitor with significant activity against multiple myeloma," Blood, vol. 102(7), pp. 2615-2622 (2003).
Pei et al., "Synergistic induction of oxidative injury and apoptosis in human multiple myeloma cells by the proteasome inhibitor bortezomib and histone deacetylase inhibitors," Clinical Cancer Research: An Official Journal of the American Association for Cancer Research, vol. 10, No. 11, pp. 3839-3852 (2004).
Hideshima et al., "Small-molecule inhibition of proteasome and aggresome function induces synergistic antitumor activity in multiple myeloma," Proceedings of the National Academy of Sciences of the United States of America, vol. 102, No. 24, pp. 8567-8572 (2005).
Mitsiades et al., "Transcriptional signature of histone deacetylase inhibition in multiple myeloma: Biological and clinical implications," Proceedings of the National Academy of Sciences of the United States of America, vol. 101, No. 2, pp. 540-545 (2004).
Maiso et al., "The Histone Deacetylase Inhibitor LBH589 is a Potent Antimyeloma Agent that Overcomes Drug Resistance," Cancer Research, vol. 66(11), pp. 5781-5789 (2006).
Remiszewski et al: N-Hydroxy-3-phenyt-2propenamides as novel inhibitors of human histone deacetylase with in vivo antitumor activity: discovery of (2E)-N-hydroxy-3-[4-[[(2-hydroxyethyl)[2-(1H-indol-3-yl)ethyl]amino]methyl]phenyl]-2-propenamide (NVP-LAQ824), Journal of Medicinal Chemistry, 2003, vol. 46, No. 21, pp. 4609-4624.
Lara et al: "Proteasome inhibition with PS-341 (Bortezomib) in lung cancer therapy", Seminars in Oncology, vol. 31, No. 1 suppl 1, pp. 40-46, Feb. 2004.
Pamaretakis et al: "Activation of Bak, Bax, and BH3—only proteins in the apoptotic response to doxorubicin", Journ of biological chemistry, 2002, vol. 277, No. 46 pp. 44317-44326.
Mitsiades et al: "Transcriptional signature of histone deacetylase inhibition in multiple myeloma: biological and clinical implications", PNAS, vol. 101, No. 2, pp. 540-545, Jan. 13, 2004.
Dacinostat [INN]RN: 404951-53-7, (abstract) [online] [retrieved Feb. 17, 2010] database ChemIDplus Advanced.

* cited by examiner

*Primary Examiner* — James D Anderson
(74) *Attorney, Agent, or Firm* — Michelle Han; Matthew E. Mulkeen

(57) ABSTRACT

The present invention relates to the use of an HDAC inhibitor, especially an HDAC inhibitor of formula (I)

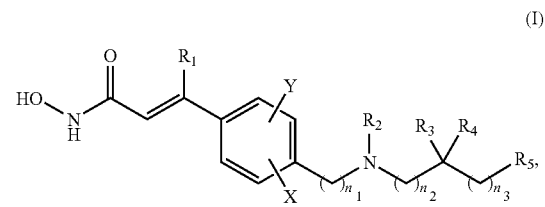

(I)

wherein the radicals and symbols have the meanings as defined in the specification, for the preparation of a medicament for the treatment of myeloma, in particular, multiple myeloma, especially myeloma which is resistant to conventional chemotherapy; to a combination comprising an HDAC inhibitor and a compound effecting apoptosis of myeloma cells, preferably bortezomib, for simultaneous, separate or sequential use; to methods of treating myeloma; and to a pharmaceutical composition comprising said combination.

2 Claims, No Drawings

USE OF HDAC INHIBITORS FOR THE TREATMENT OF MYELOMA

This is a continuation of application Ser. No. 11/996,323 filed on Jan. 21, 2008, which is National Stage of International Application No. PCT/US2006/29801 filed on Aug. 1, 2006, which claims the benefit of U.S. Provisional Application 60/705,226 filed Aug. 3, 2005, the entire disclosures of which are hereby incorporated by reference.

The present invention relates to the use of an HDAC inhibitor for the preparation of a medicament for the treatment of myeloma; a method of treating a warm-blooded animal, especially a human, having myeloma, comprising administering to said animal a therapeutically effective amount of an HDAC inhibitor, especially a compound of formula (I), as defined herein; to a combination comprising an HDAC inhibitor and a compound effecting apoptosis of myeloma cells, preferably bortezomib, and optionally at least one pharmaceutically acceptable carrier, for simultaneous, separate or sequential use; and to a pharmaceutical composition and a commercial package comprising said combination.

The term "myeloma", as used herein, relates to a tumor composed of cells of the type normally found in the bone marrow. The term "multiple myeloma", as used herein, means a disseminated malignant neoplasm of plasma cells which is characterized by multiple bone marrow tumor foci and secretion of an M component (a monoclonal immunoglobulin fragment), associated with widespread osteolytic lesions resulting in bone pain, pathologic fractures, hypercalaemia and normochromic normocytic anaemia. Multiple myeloma is incurable by the use of conventional and high dose chemotherapies.

The compounds of formula (I), as defined herein, are histone deacetylase inhibitors ("HDAC inhibitors"). Reversible acetylation of histones is a major regulator of gene expression that acts by altering accessibility of transcription factors to DNA. In normal cells, histone deacetylase (HDA) and histone acetyltransferase together control the level of acetylation of histones to maintain a balance. Inhibition of HDA results in the accumulation of hyperacetylated histones, which results in a variety of cellular responses.

Surprisingly, it was now found that HDAC inhibitors, especially the compounds of formula (I), as defined herein, directly inhibit the proliferation of myeloma cell lines and patient myeloma cells that express Flt-1. In addition, such compounds inhibit myeloma cell migration, assayed via transwell cell migration assay. Furthermore, such compounds, can inhibit both proliferation of myeloma cells that are adherent to bone marrow stromal cells (BMSCs), and the secretion of IL-6 induced by binding of myeloma cells to BMSCs.

Hence, the invention relates to the use of an HDAC inhibitor for the preparation of a medicament for the treatment of myeloma.

HDAC Inhibitor Compounds

HDAC inhibitor compounds of particular interest for use in the inventive combination are hydroxamate compounds described by the formula (I):

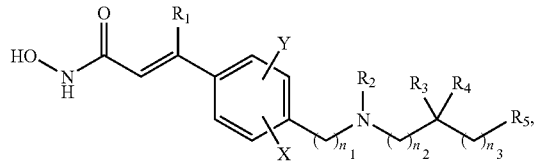

(I)

wherein
$R_1$ is H; halo; or a straight-chain $C_1$-$C_6$alkyl, especially methyl, ethyl or n-propyl, which methyl, ethyl and n-propyl substituents are unsubstituted or substituted by one or more substituents described below for alkyl substituents;

$R_2$ is selected from H; $C_1$-$C_{10}$alkyl, preferably $C_1$-$C_6$alkyl, e.g., methyl, ethyl or —$CH_2CH_2$—OH; $C_4$-$C_9$cycloalkyl; $C_4$-$C_9$heterocycloalkyl; $C_4$-$C_9$heterocycloalkylalkyl; cycloalkylalkyl, e.g., cyclopropylmethyl; aryl; heteroaryl; arylalkyl, e.g., benzyl; heteroarylalkyl, e.g., pyridylmethyl; —$(CH_2)_nC(O)R_6$; —$(CH_2)_nOC(O)R_6$; amino acyl; HON—C(O)—CH=C($R_1$)-aryl-alkyl-; and —$(CH_2)_nR_7$;

$R_3$ and $R_4$ are the same or different and, independently, H; $C_1$-$C_6$alkyl; acyl; or acylamino, or $R_3$ and $R_4$, together with the carbon to which they are bound, represent C=O, C=S or C=$NR_8$, or $R_2$, together with the nitrogen to which it is bound, and $R_3$, together with the carbon to which it is bound, can form a $C_4$-$C_9$heterocycloalkyl; a heteroaryl; a polyheteroaryl; a non-aromatic polyheterocycle; or a mixed aryl and non-aryl polyheterocycle ring;

$R_5$ is selected from H; $C_1$-$C_6$alkyl; $C_4$-$C_9$cycloalkyl; $C_4$-$C_9$heterocycloalkyl; acyl; aryl; heteroaryl; arylalkyl, e.g., benzyl; heteroarylalkyl, e.g., pyridylmethyl; aromatic polycycles; non-aromatic polycycles; mixed aryl and non-aryl polycycles; polyheteroaryl; non-aromatic polyheterocycles; and mixed aryl and non-aryl polyheterocycles;

$n$, $n_1$, $n_2$ and $n_3$ are the same or different and independently selected from 0-6, when $n_1$ is 1-6, each carbon atom can be optionally and independently substituted with $R_3$ and/or $R_4$;

X and Y are the same or different and independently selected from H; halo; $C_1$-$C_4$alkyl, such as $CH_3$ and $CF_3$; $NO_2$; $C(O)R_1$; $OR_9$; $SR_9$; CN; and $NR_{10}R_{11}$;

$R_6$ is selected from H; $C_1$-$C_6$alkyl; $C_4$-$C_9$cycloalkyl; $C_4$-$C_9$heterocycloalkyl; cycloalkylalkyl, e.g., cyclopropylmethyl; aryl; heteroaryl; arylalkyl, e.g., benzyl and 2-phenylethenyl; heteroarylalkyl, e.g., pyridylmethyl; $OR_{12}$; and $NR_{13}R_{14}$;

$R_7$ is selected from $OR_{15}$; $SR_{15}$; $S(O)R_{16}$; $SO_2R_{17}$; $NR_{13}R_{14}$; and $NR_{12}SO_2R_6$;

$R_8$ is selected from H; $OR_{15}$; $NR_{13}R_{14}$; $C_1$-$C_6$alkyl; $C_4$-$C_9$cycloalkyl; $C_4$-$C_9$heterocycloalkyl; aryl; heteroaryl; arylalkyl, e.g., benzyl; and heteroarylalkyl, e.g., pyridylmethyl;

$R_9$ is selected from $C_1$-$C_4$alkyl, e.g., $CH_3$ and $CF_3$; C(O)-alkyl, e.g., C(O)$CH_3$; and C(O)$CF_3$;

$R_{10}$ and $R_{11}$ are the same or different and independently selected from H; $C_1$-$C_4$alkyl; and —C(O)-alkyl;

$R_{12}$ is selected from H; $C_1$-$C_6$alkyl; $C_4$-$C_9$cycloalkyl; $C_4$-$C_9$heterocycloalkyl; $C_4$-$C_9$heterocycloalkylalkyl; aryl; mixed aryl and non-aryl polycycle; heteroaryl; arylalkyl, e.g., benzyl; and heteroarylalkyl, e.g., pyridylmethyl;

$R_{13}$ and $R_{14}$ are the same or different and independently selected from H; $C_1$-$C_6$alkyl; $C_4$-$C_9$cycloalkyl; $C_4$-$C_9$heterocycloalkyl; aryl; heteroaryl; arylalkyl, e.g., benzyl; heteroarylalkyl, e.g., pyridylmethyl; amino acyl; or $R_{13}$ and $R_{14}$, together with the nitrogen to which they are bound, are $C_4$-$C_9$heterocycloalkyl; heteroaryl; polyheteroaryl; non-aromatic polyheterocycle; or mixed aryl and non-aryl polyheterocycle;

$R_{15}$ is selected from H; $C_1$-$C_6$alkyl; $C_4$-$C_9$cycloalkyl; $C_4$-$C_9$heterocycloalkyl; aryl; heteroaryl; arylalkyl; heteroarylalkyl; and $(CH_2)_m ZR_{12}$;

$R_{16}$ is selected from $C_1$-$C_6$alkyl; $C_4$-$C_9$cycloalkyl; $C_4$-$C_9$heterocycloalkyl; aryl; heteroaryl; polyheteroaryl; arylalkyl; heteroarylalkyl; and $(CH_2)_m ZR_{12}$;

$R_{17}$ is selected from $C_1$-$C_6$alkyl; $C_4$-$C_9$cycloalkyl; $C_4$-$C_9$heterocycloalkyl; aryl; aromatic polycycles; heteroaryl; arylalkyl; heteroarylalkyl; polyheteroaryl and $NR_{13}R_{14}$;

m is an integer selected from 0-6; and

Z is selected from O; $NR_{13}$; S; and S(O), or a pharmaceutically acceptable salt thereof.

As appropriate, "unsubstituted" means that there is no substituent or that the only substituents are hydrogen.

Halo substituents are selected from fluoro, chloro, bromo and iodo, preferably fluoro or chloro.

Alkyl substituents include straight- and branched-$C_1$-$C_6$alkyl, unless otherwise noted. Examples of suitable straight- and branched-$C_1$-$C_6$alkyl substituents include methyl, ethyl, n-propyl, 2-propyl, n-butyl, sec-butyl, t-butyl and the like. Unless otherwise noted, the alkyl substituents include both unsubstituted alkyl groups and alkyl groups that are substituted by one or more suitable substituents, including unsaturation, i.e., there are one or more double or triple C—C bonds; acyl; cycloalkyl; halo; oxyalkyl; alkylamino; aminoalkyl; acylamino; and $OR_{15}$, e.g., alkoxy. Preferred substituents for alkyl groups include halo, hydroxy, alkoxy, oxyalkyl, alkylamino and aminoalkyl.

Cycloalkyl substituents include $C_3$-$C_9$cycloalkyl groups, such as cyclopropyl, cyclobutyl, cyclopentyl, cyclohexyl and the like, unless otherwise specified. Unless otherwise noted, cycloalkyl substituents include both unsubstituted cycloalkyl groups and cycloalkyl groups that are substituted by one or more suitable substituents, including $C_1$-$C_6$alkyl, halo, hydroxy, aminoalkyl, oxyalkyl, alkylamino and $OR_{15}$, such as alkoxy. Preferred substituents for cycloalkyl groups include halo, hydroxy, alkoxy, oxyalkyl, alkylamino and aminoalkyl.

The above discussion of alkyl and cycloalkyl substituents also applies to the alkyl portions of other substituents, such as, without limitation, alkoxy, alkyl amines, alkyl ketones, arylalkyl, heteroarylalkyl, alkylsulfonyl and alkyl ester substituents and the like.

Heterocycloalkyl substituents include 3- to 9-membered aliphatic rings, such as 4- to 7-membered aliphatic rings, containing from 1-3 heteroatoms selected from nitrogen, sulfur, oxygen. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane and 1,4-oxathiapane. Unless otherwise noted, the rings are unsubstituted or substituted on the carbon atoms by one or more suitable substituents, including $C_1$-$C_6$alkyl; $C_4$-$C_9$cycloalkyl; aryl; heteroaryl; arylalkyl; benzyl; heteroarylalkyl, e.g., pyridylmethyl; halo; amino; alkyl amino and $OR_{15}$, e.g., alkoxy. Unless otherwise noted, nitrogen heteroatoms are unsubstituted or substituted by H, $C_1$-$C_4$alkyl; arylalkyl, e.g., benzyl; heteroarylalkyl, e.g., pyridylmethyl; acyl; aminoacyl; alkylsulfonyl; and arylsulfonyl.

Cycloalkylalkyl substituents include compounds of the formula —$(CH_2)_{n5}$-cycloalkyl, wherein n5 is a number from 1-6. Suitable alkylcycloalkyl substituents include cyclopentylmethyl, cyclopentylethyl, cyclohexylmethyl and the like. Such substituents are unsubstituted or substituted in the alkyl portion or in the cycloalkyl portion by a suitable substituent, including those listed above for alkyl and cycloalkyl.

Aryl substituents include unsubstituted phenyl and phenyl substituted by one or more suitable substituents including $C_1$-$C_6$alkyl; cycloalkylalkyl, e.g., cyclopropylmethyl; O(CO)alkyl; oxyalkyl; halo; nitro; amino; alkylamino; aminoalkyl; alkyl ketones; nitrile; carboxyalkyl; alkylsulfonyl; aminosulfonyl; arylsulfonyl and $OR_{15}$, such as alkoxy. Preferred substituents include including $C_1$-$C_6$alkyl; cycloalkyl, e.g., cyclopropylmethyl; alkoxy; oxyalkyl; halo; nitro; amino; alkylamino; aminoalkyl; alkyl ketones; nitrile; carboxyalkyl; alkylsulfonyl; arylsulfonyl and aminosulfonyl. Examples of suitable aryl groups include $C_1$-$C_4$alkylphenyl, $C_1$-$C_4$alkoxyphenyl, trifluoromethylphenyl, methoxyphenyl, hydroxyethylphenyl, dimethylaminophenyl, aminopropylphenyl, carbethoxyphenyl, methanesulfonylphenyl and tolylsulfonylphenyl.

Aromatic polycycles include naphthyl, and naphthyl substituted by one or more suitable substituents including $C_1$-$C_6$alkyl; alkylcycloalkyl, e.g., cyclopropylmethyl; oxyalkyl; halo; nitro; amino; alkylamino; aminoalkyl; alkyl ketones; nitrile; carboxyalkyl; alkylsulfonyl; arylsulfonyl; aminosulfonyl and $OR_{15}$, such as alkoxy.

Heteroaryl substituents include compounds with a 5- to 7-membered aromatic ring containing one or more heteroatoms, e.g., from 1-4 heteroatoms, selected from N, O and S. Typical heteroaryl substituents include furyl, thienyl, pyrrole, pyrazole, triazole, thiazole, oxazole, pyridine, pyrimidine, isoxazolyl, pyrazine and the like. Unless otherwise noted, heteroaryl substituents are unsubstituted or substituted on a carbon atom by one or more suitable substituents, including alkyl, the alkyl substituents identified above, and another heteroaryl substituent. Nitrogen atoms are unsubstituted or substituted, e.g., by $R_{13}$; especially useful N substituents include H, $C_1$-$C_4$alkyl, acyl, aminoacyl and sulfonyl.

Arylalkyl substituents include groups of the formula —$(CH_2)_{n5}$-aryl, —$(CH_2)_{n5-1}$—(CH-aryl)-$(CH_2)_{n5}$-aryl or —$(CH_2)_{n5-1}$CH(aryl)(aryl), wherein aryl and n5 are defined above. Such arylalkyl substituents include benzyl, 2-phenylethyl, 1-phenylethyl, tolyl-3-propyl, 2-phenylpropyl, diphenylmethyl, 2-diphenylethyl, 5,5-dimethyl-3-phenylpentyl and the like. Arylalkyl substituents are unsubstituted or substituted in the alkyl moiety or the aryl moiety or both as described above for alkyl and aryl substituents.

Heteroarylalkyl substituents include groups of the formula —$(CH_2)_{n5}$-heteroaryl, wherein heteroaryl and n5 are defined above and the bridging group is linked to a carbon or a nitrogen of the heteroaryl portion, such as 2-, 3- or 4-pyridylmethyl, imidazolylmethyl, quinolylethyl and pyrrolylbutyl. Heteroaryl substituents are unsubstituted or substituted as discussed above for heteroaryl and alkyl substituents.

Amino acyl substituents include groups of the formula —C(O)—$(CH_2)_n$—C(H)($NR_{13}R_{14}$)—$(CH_2)_n$—$R_5$, wherein n, $R_{13}$, $R_{14}$ and $R_5$ are described above. Suitable aminoacyl substituents include natural and non-natural amino acids, such as glycinyl, D-tryptophanyl, L-lysinyl, D- or L-homoserinyl, 4-aminobutryic acyl and ±-3-amin-4-hexenoyl.

Non-aromatic polycycle substituents include bicyclic and tricyclic fused ring systems where each ring can be 4- to 9-membered and each ring can contain zero, one or more double and/or triple bonds. Suitable examples of non-aromatic polycycles include decalin, octahydroindene, perhydrobenzocycloheptene and perhydrobenzo-[f]-azulene. Such substituents are unsubstituted or substituted as described above for cycloalkyl groups.

Mixed aryl and non-aryl polycycle substituents include bicyclic and tricyclic fused ring systems where each ring can be 4- to 9-membered and at least one ring is aromatic. Suitable examples of mixed aryl and non-aryl polycycles include methylenedioxyphenyl, bis-methylenedioxyphenyl, 1,2,3,4-tetrahydronaphthalene, dibenzosuberane, dihydroanthracene and 9H-fluorene. Such substituents are unsubstituted or substituted by nitro or as described above for cycloalkyl groups.

Polyheteroaryl substituents include bicyclic and tricyclic fused ring systems where each ring can independently be 5- or 6-membered and contain one or more heteroatom, e.g., 1, 2, 3 or 4 heteroatoms, chosen from O, N or S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline and the like. Unless otherwise noted, polyheteroaryl substituents are unsubstituted or substituted on a carbon atom by one or more suitable substituents, including alkyl, the alkyl substituents identified above and a substituent of the formula —O—$(CH_2CH=CH(CH_3)(CH_2))_{1-3}H$. Nitrogen atoms are unsubstituted or substituted, e.g., by $R_{13}$, especially useful N substituents include H, $C_1$-$C_4$acyl, aminoacyl and sulfonyl.

Non-aromatic polyheterocyclic substituents include bicyclic and tricyclic fused ring systems where each ring can be 4- to 9-membered, contain one or more heteroatom, e.g., 1, 2, 3 or 4 heteroatoms, chosen from O, N or S and contain zero or one or more C—C double or triple bonds. Suitable examples of non-aromatic polyheterocycles include hexitol, cis-perhydro-cyclohepta[b]pyridinyl, decahydro-benzo[f][1,4]oxazepinyl, 2,8-dioxabicyclo[3.3.0]octane, hexahydro-thieno[3,2-b]thiophene, perhydropyrrolo[3,2-b]pyrrole, perhydronaphthyridine, perhydro-1H-dicyclopenta[b,e]pyran. Unless otherwise noted, non-aromatic polyheterocyclic substituents are unsubstituted or substituted on a carbon atom by one or more substituents, including alkyl and the alkyl substituents identified above. Nitrogen atoms are unsubstituted or substituted, e.g., by $R_{13}$, especially useful N substituents include H, $C_1$-$C_4$alkyl, acyl, aminoacyl and sulfonyl.

Mixed aryl and non-aryl polyheterocycles substituents include bicyclic and tricyclic fused ring systems where each ring can be 4- to 9-membered, contain one or more heteroatom chosen from O, N or S, and at least one of the rings must be aromatic. Suitable examples of mixed aryl and non-aryl polyheterocycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydro-pyrido[2,3-b][1,4]diazepin-4-one, 1,2,3,4,6,11-hexahydro-benzo[b]pyrido[2,3-e][1,4]diazepin-5-one. Unless otherwise noted, mixed aryl and non-aryl polyheterocyclic substituents are unsubstituted or substituted on a carbon atom by one or more suitable substituents including —N—OH, =N—OH, alkyl and the alkyl substituents identified above. Nitrogen atoms are unsubstituted or substituted, e.g., by $R_{13}$; especially useful N substituents include H, $C_1$-$C_4$alkyl, acyl, aminoacyl and sulfonyl.

Amino substituents include primary, secondary and tertiary amines and in salt form, quaternary amines. Examples of amino substituents include mono- and di-alkylamino, mono- and di-aryl amino, mono- and di-arylalkyl amino, aryl-arylalkylamino, alkyl-arylamino, alkyl-arylalkylamino and the like.

Sulfonyl substituents include alkylsulfonyl and arylsulfonyl, e.g., methane sulfonyl, benzene sulfonyl, tosyl and the like.

Acyl substituents include groups of formula —C(O)—W, —OC(O)—W, —C(O)—O—W or —C(O)NR$_{13}$R$_{14}$, where W is $R_{16}$, H or cycloalkylalkyl.

Acylamino substituents include substituents of the formula —N(R$_{12}$)C(O)—W, —N(R$_{12}$)C(O)—O—W and —N(R$_{12}$)C(O)—NHOH and $R_{12}$ and W are defined above.

The $R_2$ substituent HON—C(O)—CH=C($R_1$)-aryl-alkyl- is a group of the formula

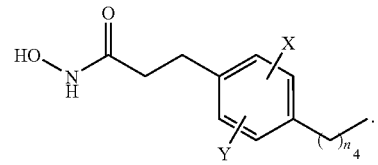

Preferences for each of the substituents include the following:
$R_1$ is H, halo or a straight-chain $C_1$-$C_4$alkyl;
$R_2$ is selected from H, $C_1$-$C_6$alkyl, $C_4$-$C_9$cycloalkyl, $C_4$-$C_9$heterocycloalkyl, cycloalkylalkyl, aryl, heteroaryl, arylalkyl, heteroarylalkyl, —(CH$_2$)$_n$C(O)R$_6$, amino acyl and —(CH$_2$)$_n$R$_7$;
$R_3$ and $R_4$ are the same or different and independently selected from H and $C_1$-$C_6$alkyl, or
$R_3$ and $R_4$, together with the carbon to which they are bound, represent C=O, C=S or C=NR$_8$,
$R_5$ is selected from H, $C_1$-$C_6$alkyl, $C_4$-$C_9$cycloalkyl, $C_4$-$C_9$heterocycloalkyl, aryl, heteroaryl, arylalkyl, heteroarylalkyl, a aromatic polycycle, a non-aromatic polycycle, a mixed aryl and non-aryl polycycle, polyheteroaryl, a non-aromatic polyheterocycle, and a mixed aryl and non-aryl polyheterocycle;
n, $n_1$, $n_2$ and $n_3$ are the same or different and independently selected from 0-6, when $n_1$ is 1-6, each carbon atom is unsubstituted or independently substituted with $R_3$ and/or $R_4$;
X and Y are the same or different and independently selected from H, halo, $C_1$-$C_4$alkyl, CF$_3$, NO$_2$, C(O)R$_1$, OR$_9$, SR$_9$, CN and NR$_{10}$R$_{11}$;
$R_6$ is selected from H, $C_1$-$C_6$alkyl, $C_4$-$C_9$cycloalkyl, $C_4$-$C_9$heterocycloalkyl, alkylcycloalkyl, aryl, heteroaryl, arylalkyl, heteroarylalkyl, OR$_{12}$ and NR$_{13}$R$_{14}$;
$R_7$ is selected from OR$_{15}$, SR$_{15}$, S(O)R$_{16}$, SO$_2$R$_{17}$, NR$_{13}$R$_{14}$ and NR$_{12}$SO$_2$R$_6$;
$R_8$ is selected from H, OR$_{15}$, NR$_{13}$R$_{14}$, $C_1$-$C_6$alkyl, $C_4$-$C_9$cycloalkyl, $C_4$-$C_9$heterocycloalkyl, aryl, heteroaryl, arylalkyl and heteroarylalkyl;
$R_9$ is selected from $C_1$-$C_4$alkyl and C(O)-alkyl;
$R_{10}$ and $R_{11}$ are the same or different and independently selected from H, $C_1$-$C_4$alkyl and —C(O)-alkyl;
$R_{12}$ is selected from H, $C_1$-$C_6$alkyl, $C_4$-$C_9$cycloalkyl, $C_4$-$C_9$heterocycloalkyl, aryl, heteroaryl, arylalkyl and heteroarylalkyl;
$R_{13}$ and $R_{14}$ are the same or different and independently selected from H, $C_1$-$C_6$alkyl, $C_4$-$C_9$cycloalkyl, $C_4$-$C_9$heterocycloalkyl, aryl, heteroaryl, arylalkyl, heteroarylalkyl and amino acyl;
$R_{15}$ is selected from H, $C_1$-$C_6$alkyl, $C_4$-$C_9$cycloalkyl, $C_4$-$C_9$heterocycloalkyl, aryl, heteroaryl, arylalkyl, heteroarylalkyl and (CH$_2$)$_m$ZR$_{12}$;
$R_{16}$ is selected from $C_1$-$C_6$alkyl, $C_4$-$C_9$cycloalkyl, $C_4$-$C_9$heterocycloalkyl, aryl, heteroaryl, arylalkyl, heteroarylalkyl and (CH$_2$)$_m$ZR$_{12}$;
$R_{17}$ is selected from $C_1$-$C_6$alkyl, $C_4$-$C_9$cycloalkyl, $C_4$-$C_9$heterocycloalkyl, aryl, heteroaryl, arylalkyl, heteroarylalkyl and NR$_{13}$R$_{14}$;
m is an integer selected from 0-6; and
Z is selected from O, NR$_{13}$, S and S(O);
or a pharmaceutically acceptable salt thereof.

Useful compounds of the formula (I), include those wherein each of $R_1$, X, Y, $R_3$ and $R_4$ is H, including those wherein one of $n_2$ and $n_3$ is 0 and the other is 1, especially those wherein $R_2$ is H or —$CH_2$—$CH_2$—OH.

One suitable genus of hydroxamate compounds are those of formula (Ia)

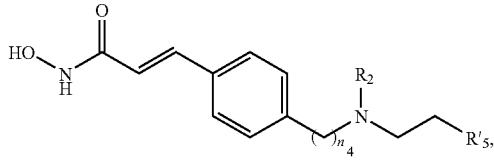

(Ia)

wherein
  $n_4$ is 0-3;
  $R_2$ is selected from H, $C_1$-$C_6$alkyl, $C_4$-$C_9$cycloalkyl, $C_4$-$C_9$heterocycloalkyl, cycloalkylalkyl, aryl, heteroaryl, arylalkyl, heteroarylalkyl, —$(CH_2)_nC(O)R_6$, amino acyl and —$(CH_2)_nR_7$; and
  $R_5$ is heteroaryl; heteroarylalkyl, e.g., pyridylmethyl; aromatic polycycles; non-aromatic polycycles; mixed aryl and non-aryl polycycles; polyheteroaryl or mixed aryl; and non-aryl polyheterocycles;
or a pharmaceutically acceptable salt thereof.

Another suitable genus of hydroxamate compounds are those of formula (Ia)

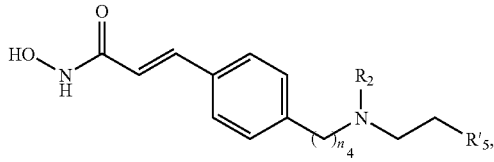

(Ia)

wherein
  $n_4$ is 0-3;
  $R_2$ is selected from H, $C_1$-$C_6$alkyl, $C_4$-$C_9$cycloalkyl, $C_4$-$C_9$heterocycloalkyl, cycloalkylalkyl, aryl, heteroaryl, arylalkyl, heteroarylalkyl, —$(CH_2)_nC(O)R_6$, amino acyl and —$(CH_2)_nR_7$;
  $R_5$ is aryl; arylalkyl; aromatic polycycles; non-aromatic polycycles and mixed aryl; and non-aryl polycycles, especially aryl, such as p-fluorophenyl, p-chlorophenyl, p-O—$C_1$-$C_4$alkylphenyl, such as p-methoxyphenyl, and p-$C_1$-$C_4$alkylphenyl; and arylalkyl, such as benzyl, ortho-, meta- or para-fluorobenzyl, ortho-, meta- or para-chlorobenzyl, ortho-, meta- or para-mono, di- or tri-O—$C_1$-$C_4$alkylbenzyl, such as ortho-, meta- or para-methoxybenzyl, m,p-diethoxybenzyl, o,m,p-trimethoxybenzyl and ortho-, meta- or para-mono, di- or tri-$C_1$-$C_4$alkylphenyl, such as p-methyl, m,m-diethylphenyl;
or a pharmaceutically acceptable salt thereof.

Another interesting genus is the compounds of formula (Ib)

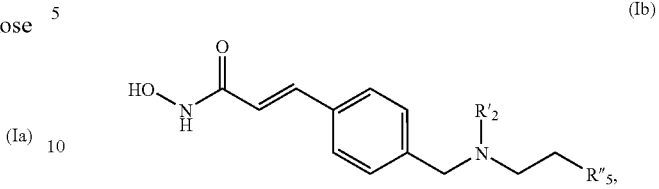

(Ib)

wherein
  $R_2$ is selected from H; $C_1$-$C_6$alkyl; $C_4$-$C_6$cycloalkyl; cycloalkylalkyl, e.g., cyclopropylmethyl; $(CH_2)_{2-4}OR_{21}$, where $R_{21}$ is H, methyl, ethyl, propyl and i-propyl; and
  $R_5$ is unsubstituted 1H-indol-3-yl, benzofuran-3-yl or quinolin-3-yl, or substituted 1H-indol-3-yl, such as 5-fluoro-1H-indol-3-yl or 5-methoxy-1H-indol-3-yl, benzofuran-3-yl or quinolin-3-yl;
or a pharmaceutically acceptable salt thereof.

Another interesting genus of hydroxamate compounds are the compounds of formula (Ic)

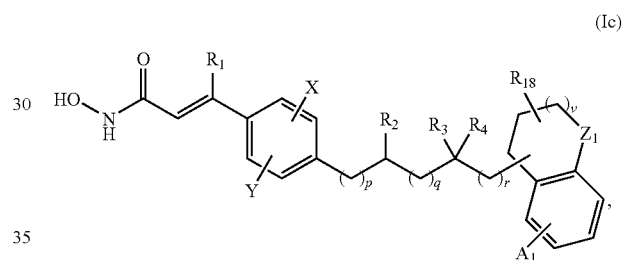

(Ic)

wherein
  the ring containing $Z_1$ is aromatic or non-aromatic, which non-aromatic rings are saturated or unsaturated,
  $Z_1$ is O, S or N—$R_{20}$;
  $R_{18}$ is H; halo; $C_1$-$C_6$alkyl (methyl, ethyl, t-butyl); $C_3$-$C_7$cycloalkyl; aryl, e.g., unsubstituted phenyl or phenyl substituted by 4-$OCH_3$ or 4-$CF_3$; or heteroaryl, such as 2-furanyl, 2-thiophenyl or 2-, 3- or 4-pyridyl;
  $R_{20}$ is H; $C_1$-$C_6$alkyl; $C_1$-$C_6$alkyl-$C_3$-$C_9$cycloalkyl, e.g., cyclopropylmethyl; aryl; heteroaryl; arylalkyl, e.g., benzyl; heteroarylalkyl, e.g., pyridylmethyl; acyl, e.g., acetyl, propionyl and benzoyl; or sulfonyl, e.g., methanesulfonyl, ethanesulfonyl, benzenesulfonyl and toluenesulfonyl;
  $A_1$ is 1, 2 or 3 substituents which are independently H; $C_1$-$C_6$alkyl; —$OR_{19}$; halo; alkylamino; aminoalkyl; halo; or heteroarylalkyl, e.g., pyridylmethyl;
  $R_{19}$ is selected from H; $C_1$-$C_6$alkyl; $C_4$-$C_9$cycloalkyl; $C_4$-$C_9$heterocycloalkyl; aryl; heteroaryl; arylalkyl, benzyl; heteroarylalkyl, e.g., pyridylmethyl and —$(CH_2CH=CH(CH_3)(CH_2))_{1-3}H$;
  $R_2$ is selected from H, $C_1$-$C_6$alkyl, $C_4$-$C_9$cycloalkyl, $C_4$-$C_9$heterocycloalkyl, cycloalkylalkyl, aryl, heteroaryl, arylalkyl, heteroarylalkyl, —$(CH_2)_nC(O)R_6$, amino acyl and —$(CH_2)_nR_7$;
  v is 0, 1 or 2;
  p is 0-3; and
  q is 1-5 and r is 0; or
  q is 0 and r is 1-5;
or a pharmaceutically acceptable salt thereof. The other variable substituents are as defined above.

Especially useful compounds of formula (Ic), are those wherein $R_2$ is H, or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3, especially those wherein $Z_1$ is N—$R_{20}$. Among these compounds $R_2$ is preferably H or —$CH_2$—$CH_2$—OH and the sum of q and r is preferably 1.

Another interesting genus of hydroxamate compounds are the compounds of formula (Id)

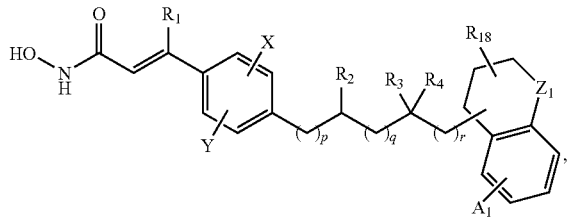

wherein
$Z_1$ is O, S or N—$R_{20}$;
$R_{18}$ is H; halo; $C_1$-$C_6$alkyl (methyl, ethyl, t-butyl); $C_3$-$C_7$cycloalkyl; aryl, e.g., unsubstituted phenyl or phenyl substituted by 4-$OCH_3$ or 4-$CF_3$; or heteroaryl;
$R_{20}$ is H; $C_1$-$C_6$alkyl, $C_1$-$C_6$alkyl-$C_3$-$C_9$cycloalkyl, e.g., cyclopropylmethyl; aryl; heteroaryl; arylalkyl, e.g., benzyl; heteroarylalkyl, e.g., pyridylmethyl; acyl, e.g., acetyl, propionyl and benzoyl; or sulfonyl, e.g., methanesulfonyl, ethanesulfonyl, benzenesulfonyl, toluenesulfonyl);
$A_1$ is 1, 2 or 3 substituents which are independently H, $C_1$-$C_6$alkyl, —$OR_{19}$ or halo;
$R_{19}$ is selected from H; $C_1$-$C_6$alkyl; $C_4$-$C_9$cycloalkyl; $C_4$-$C_9$heterocycloalkyl; aryl; heteroaryl; arylalkyl, e.g., benzyl; and heteroarylalkyl, e.g., pyridylmethyl;
p is 0-3; and
q is 1-5 and r is 0; or
q is 0 and r is 1-5;
or a pharmaceutically acceptable salt thereof. The other variable substituents are as defined above.

Especially useful compounds of formula (Id), are those wherein $R_2$ is H or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3. Among these compounds $R_2$ is preferably H or —$CH_2$—$CH_2$—OH and the sum of q and r is preferably 1.

The present invention further relates to compounds of the formula (Ie)

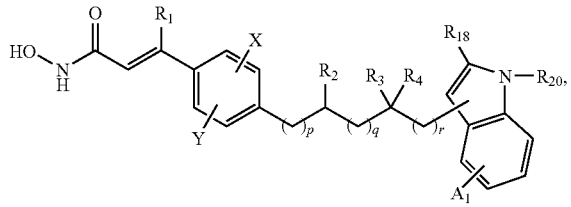

or a pharmaceutically acceptable salt thereof. The variable substituents are as defined above.

Especially useful compounds of formula (Ie), are those wherein $R_{18}$ is H, fluoro, chloro, bromo, a $C_1$-$C_4$alkyl group, a substituted $C_1$-$C_4$alkyl group, a $C_3$-$C_7$cycloalkyl group, unsubstituted phenyl, phenyl substituted in the para-position, or a heteroaryl, e.g., pyridyl, ring.

Another group of useful compounds of formula (Ie), are those wherein $R_2$ is H or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3. Among these compounds $R_2$ is preferably H or —$CH_2$—$CH_2$—OH and the sum of q and r is preferably 1. Among these compounds p is preferably 1 and $R_3$ and $R_4$ are preferably H.

Another group of useful compounds of formula (Ie), are those wherein $R_{18}$ is H, methyl, ethyl, t-butyl, trifluoromethyl, cyclohexyl, phenyl, 4-methoxyphenyl, 4-trifluoromethylphenyl, 2-furanyl, 2-thiophenyl, or 2-, 3- or 4-pyridyl wherein the 2-furanyl, 2-thiophenyl and 2-, 3- or 4-pyridyl substituents are unsubstituted or substituted as described above for heteroaryl rings; $R_2$ is H or —$(CH_2)_pCH_2OH$, wherein p is 1-3; especially those wherein $R_1$ is H and X and Y are each H, and wherein q is 1-3 and r is 0 or wherein q is 0 and r is 1-3. Among these compounds $R_2$ is preferably H or —$CH_2$—$CH_2$—OH and the sum of q and r is preferably 1.

Those compounds of formula (Ie), wherein $R_{20}$ is H or $C_1$-$C_6$alkyl, especially H, are important members of each of the subgenuses of compounds of formula (Ie) described above.

N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(1H-indol-3-yl)ethyl]-amino]methyl]phenyl]-2E-2-propenamide and N-hydroxy-3-[4-[[[2-(2-methyl-1H-indol-3-yl)-ethyl]-amino]methyl]phenyl]-2E-2-propenamide or a pharmaceutically acceptable salt thereof, are important compounds of formula (Ie).

The present invention further relates to the compounds of the formula (If)

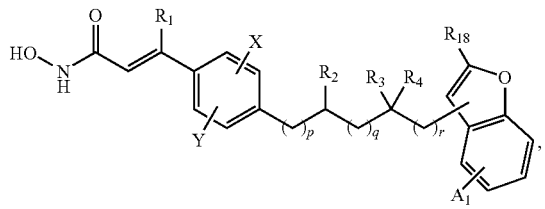

or a pharmaceutically acceptable salt thereof. The variable substituents are as defined above.

Useful compounds of formula (If), are include those wherein $R_2$ is H or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3. Among these compounds $R_2$ is preferably H or —$CH_2$—$CH_2$—OH and the sum of q and r is preferably 1.

N-hydroxy-3-[4-[[[2-(benzofur-3-yl)-ethyl]-amino]methyl]phenyl]-2E-2-propenamide or a pharmaceutically acceptable salt thereof, is an important compound of formula (If).

The compounds described above are often used in the form of a pharmaceutically acceptable salt. Pharmaceutically acceptable salts include, when appropriate, pharmaceutically acceptable base addition salts and acid addition salts, for example, metal salts, such as alkali and alkaline earth metal salts, ammonium salts, organic amine addition salts and amino acid addition salts and sulfonate salts. Acid addition salts include inorganic acid addition salts, such as hydrochloride, sulfate and phosphate; and organic acid addition salts, such as alkyl sulfonate, arylsulfonate, acetate, maleate, fumarate, tartrate, citrate and lactate. Examples of metal salts are alkali metal salts, such as lithium salt, sodium salt and potassium salt; alkaline earth metal salts, such as magnesium salt and calcium salt, aluminum salt and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

Additional HDAI compounds within the scope of formula (I), and their synthesis, are disclosed in WO 02/22577 published Mar. 21, 2002 which is incorporated herein by reference in its entirety. Two preferred compounds within the scope of WO 02/22577 are

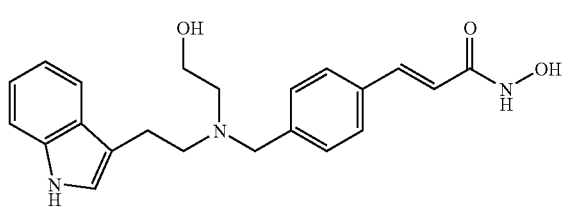

(II)

N-hydroxy-3-[4-[(2-hydroxyethyl){2-(1H-indol-3-yl)ethyl]-amino]methyl]phenyl]-2E-2-propenamide, or a pharmaceutically acceptable salt thereof; and

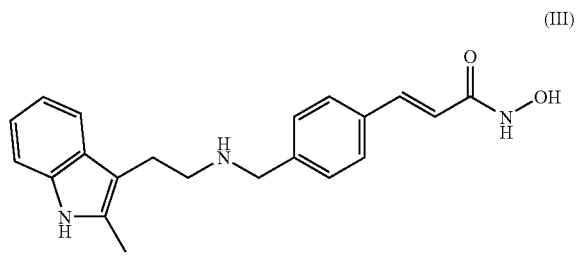

(III)

N-hydroxy-3-[4-[[[2-(2-methyl-1H-indol-3-yl)-ethyl]-amino]methyl]phenyl]-2E-2-propenamide, or a pharmaceutically acceptable salt thereof.

The present invention pertains in particular to the use of HDAC inhibitors for the preparation of a medicament for the treatment of myeloma, which is resistant to conventional chemotherapy.

An HDAC inhibitor as used for the present invention displays in the assay described above preferably an $IC_{50}$ value between 50 and 2,500 nM, more preferably between 250 and 2,000 nM, and most preferably between 500 and 1,250 nM.

Furthermore, the invention relates to a method of treating myeloma, especially myeloma which is resistant to conventional chemotherapy, comprising administering a therapeutically effective amount of an HDAC inhibitor to a warm-blooded animal, in particular, a human, in need thereof, preferably a therapeutically effective amount of a compound of formula (I), as defined above, or the salt of such compound having at least one salt-forming group, to a warm-blooded animal, preferably a human, in need thereof.

Throughout the present specification and claims myeloma means preferably multiple myeloma (MM).

The term "treatment", as used herein, comprises the treatment of patients having myeloma or being in a pre-stage of said disease which effects the delay of progression of the disease in said patients.

Bortezomib is a principle agent for the treatment of MM effecting apoptosis of myeloma cells. Surprisingly it was found that HDAC inhibitors of the present invention adds to the effect of Bortezomib on MM cells.

Hence, the present invention pertains also to a combination comprising an HDAC inhibitor, preferably a compound of formula (I), as defined above, and a compound effecting apoptosis of myeloma cells, in which the active ingredients are present in each case in free form or in the form of a pharmaceutically acceptable salt and optionally at least one pharmaceutically acceptable carrier, for simultaneous, separate or sequential use, especially for use in a method of treating myeloma. Preferably, in such combination the compound effecting apoptosis of myeloma cells is bortezomib.

A combination comprising an HDAC inhibitor and a compound effecting apoptosis of myeloma cells, in which the active ingredients are present in each case in free form or in the form of a pharmaceutically acceptable salt and optionally at least one pharmaceutically acceptable carrier, will be referred to hereinafter as a COMBINATION OF THE INVENTION.

The COMBINATION OF THE INVENTION can be a combined preparation or a pharmaceutical composition.

The term "a combined preparation", as used herein, defines especially a "kit of parts" in the sense that the active ingredients as defined above can be dosed independently or by use of different fixed combinations with distinguished amounts of the ingredients, i.e., simultaneously or at different time points. The parts of the kit can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular, a synergism, e.g., a more than additive effect, additional advantageous effects, less side effects, a combined therapeutical effect in a non-effective dosage of one or both of the first and second active ingredient, and especially a strong synergism the first and second active ingredient.

Additionally, the present invention provides a method of treating myeloma comprising administering a COMBINATION OF THE INVENTION in an amount which is jointly therapeutically effective against myeloma to a warm-blooded animal in need thereof.

The person skilled in the pertinent art is fully enabled to select relevant test models to prove the hereinbefore and hereinafter mentioned beneficial effects on myeloma of a compound inhibiting the HDAC activity or of a COMBINATION OF THE INVENTION. The pharmacological activity of a compound inhibiting the HDAC activity or a COMBI- NATION OF THE INVENTION may, e.g., be demonstrated in a suitable clinical study or by means of the Examples described below. Suitable clinical studies are, e.g., open label non-randomized, dose escalation studies in patients with advanced myeloma. Such studies prove in particular the synergism observed with the COMBINATIONS OF THE INVENTION. The beneficial effects on myeloma can be determined directly through the results of such studies or by changes in the study design which are known as such to a person skilled in the art. For example, one combination partner can be administered with a fixed dose and the dose of a second combination partner is escalated until the Maximum Tolerated Dosage (MTD) is reached. Alternatively, a placebo-controlled, double-blind study can be conducted in order to prove the benefits of the COMBINATION OF THE INVENTION mentioned herein.

EXAMPLES

HDAC Inhibitor

N-hydroxy-3-[4-[[[2-(2-methyl-1H-indol-3-yl)-ethyl]-amino]methyl]phenyl]-2E-2-propenamide, Compound (III) (Novartis Pharma, Basel, Switzerland) was dissolved in de-iodinized water and stored at −20° C., then thawed and diluted in media for cell culture experiments. For animal experiments, the drug was dissolved in sterile water prior to intraperitoneal injection.

MM-Derived Cell Lines and Patient Cells

Bortezomib-sensitive (MM.1S) and Bortezomib-resistant (MM.1R) human MM cell lines, as well as RPMI-8226 cells resistant to Doxorubicin (Dox 40), Mitoxantrone (MR20), and Melphalan (LR5), were cultured in RPMI-1640 media (Cellgro, Mediatech, VA) with 10% fetal bovine serum, 2 mmol/L L-glutamine (GIBCO, Grand Island, N.Y.), 100 U/mL penicillin, and 100 mg/mL streptomycin (GIBCO). Drug-resistant cell lines were cultured with either doxorubicin, mitoxantrone, melphalan or bortezomib to confirm their lack of drug sensitivity. MM patient cells were purified (>95% CD138+) by positive selection with anti-CD138 MACS Microbeads (Miltenyi, San Diego, Calif.). Bone marrow mononuclear cell (BMMC) and peripheral blood mononuclear cell (PBMC) specimens were obtained by Ficoll-Hipaque density sedimentation, and incubated in 96-well plates with or without Compound (III).

BMSC Cultures

Bone marrow specimens were obtained from patients with MM. Mononuclear cells, separated by FicoII-Hipaque density sedimentation, were used to establish long-term BM cultures. When an adherent cell monolayer had developed, cells were harvested in HBSS containing 0.25% trypsin and 0.02% EDTA and were washed and collected by centrifugation. The BMSCs were then plated onto flat-bottom 96-well plates overnight, and then $3\times10^4$ mM.1S cells were added for 48 hours. 150 µL of supernatant was removed and cells were pulsed with [3H]thymidine (0.5 µCi/well) during the last 8 hours of 48-hour cultures. Duoset ELISA (R&D System) was used to measure IL-6 in supernatants of 48-hour cultures of BMSCs with or without MM.1S cells, in the presence or absence of Compound (III).

DNA Synthesis

MM cells ($3\times10^4$ cells/well) were incubated in 96-well culture plates (Costar, Cambridge, Mass.) in the presence of media, Compound (III), and/or bortezomib or recombinant IL-6 (Genetics Institute, Cambridge, Mass.) for 48 hours at 37° C. DNA synthesis was measured by 3H-thymidine (NEN Products, Boston, Mass.) uptake. Cells were pulsed with 3H-thymidine (0.5 µCi/well) during the last 8 hours of 48-hour cultures. All of the experiments were performed in triplicate.

Growth Inhibition Assay

The inhibitory effect of Compound (III) on MM and BMSC growth was assessed by measuring MTS (Promega, Madison, Wis.) dye absorbance of the cells. Cells from 24-, 48- or 72-hour cultures in 200 µL media plus drug were pulsed with 40 µL of 5 mg/mL MTS to each well for the last 4 hours of the cultures. Absorbance was measured at 490 nm using a spectrophotometer (Molecular Devices Corp., Sunnyvale, Calif.).

Cell Cycle Analysis

MM cell lines and patient MM cells cultured for 0, 8, 12, 18, 36 and 42 hours in Compound (III) (1 µM), Compound (III) plus pan-caspase inhibitor ZVAD-FMK (20 µM) (Calbiochem, San Diego, Calif.), or control media, were harvested, washed with PBS, fixed with 70% ethanol and treated with 10 mg/mL RNase (Roche Diagnostics Corp., Indianapolis, Ind.). Cells were then stained with 5 mg/mL propidium iodide (Sigma), and cell cycle profile was determined using the program M software on an Epics flow cytometer (Coulter Immunology, Hialeah, Fla.). Data were analyzed using the Phoenix flow system.

Detection of Apoptosis

In addition to identifying sub-G1 cells using cell cycle analysis as described above, apoptosis was also confirmed by using annexin V staining. MM cells were cultured in media alone, or with media plus 1 µM Compound (III) at 37° C. for 24 hours. Cells were then washed twice with ice-cold PBS and resuspended ($1\times10^6$ cells/mL) in binding buffer (10 mmol/L HEPES, pH 7.4, 140 mmol/L NaCl, 2.5 mmol/L $CaCl_2$). MM cells ($1\times10^5$) were incubated with annexin V-FITC (5 µL; Pharmingen, San Diego, Calif.) and PI (5 mg/mL) for 15 minutes at room temperature. Annexin V+PI-apoptotic cells were enumerated by using the Epics cell sorter (Coulter).

Immunoblotting

Patient MM cells and MM.1S cells were cultured with 0.01, 0.1 or 1 µM Compound (III); harvested; washed; and lysed using lysis buffer: RIPA buffer, 2 mmol/L $Na_3VO_4$, 5 mmol/L NaF, 1 mmol/L phenylmethyl sulfonyl fluoride (PMSF), 5 mg/mL leupeptin and 5 mg/mL aprotinin. Cell lysates were subjected to SDS-PAGE, transferred to polyvinylidene difluoride (PVDF) membrane, and immunoblotted with anti-acetylated histone (Upstate Biotechnology, Lake Placid, N.Y.), anti-p21 antibody (Santa Cruz Biotech, Santa Cruz, Calif.), anti-PARP; anti-caspase-8, anti-caspase-9 and anti-caspase 3 (Cell Signaling, MA); as well as anti-polyubiquitin conjugates, anti-LMP7, anti-β5 (Affiniti, Mamhead, Exeter, Devon, UK). Membranes were stripped and re-probed with anti-tubulin or anti-β-actin (Sigma, St Louis, Mo.) to ensure equivalent protein loading.

Proteasome Activity Assay

Proteasome activity in cytosolic extracts was quantified using the fluorogenic proteasome substrate Suc-LLVYAMC (Calbiochem, San Diego, Calif.). Briefly, cytosolic extract (100 µg of protein in 5 µL) was incubated in a 200 µL reaction containing 20 mM Tris-HCl (pH 7.8), 0.5 mM EDTA, and 100 µM Suc-LLVY-AMC at room temperature for 90 minutes. Fluorescence was measured in a microtiter plate fluorometer (excitation, 360 nm; emission, 460 nm).

EMSA

Nuclear extracts for EMSAs were carried out. Double-stranded NF-κB consensus oligonucleotide probe (5'-GGG-GACTTTCCC-3', Santa Cruz Biotechnology) was end-labeled with [γ-32P]ATP (50 µCi at 222 TBq/mM; NEN, Boston, Mass.). Binding reactions containing 1 ng of oligonucleotide and 5 μg of nuclear protein were conducted at room temperature for 20 minutes in a total volume of 10 mL of binding buffer [10 mM Tris-HCl (pH 7.5), 50 mM NaCl, 1 mM MgCl2, 0.5 mM EDTA, 0.5 mM DTT, 4% glycerol (v/v), and 0.5 mg of poly (dl.dC) (Pharmacia, Peapack, N.J.).

Xenograft Murine Model

Five- to six-week-old Beige-Nude-Xid mice were inoculated subcutaneously into the right flank with $3\times10^7$ MM cells in 100 μL of RPMI 1640, together with 100 μL of Matrigel basement membrane matrix (Becton Dickinson, Bedford, Mass.) as previously described. When tumors were measurable, mice were assigned into one group receiving Compound (III) 25 mg/kg i.p. daily or into a control group receiving the vehicle alone (0.9% sodium chloride) at the same schedule. Treatment with Compound (III) was given at 25 mg/kg. Caliper measurements of the longest perpendicular tumor diameters were performed every alternate day to estimate the tumor volume, using the following formula:

$$4\pi/3 \times (width/2)2 \times (length/2),$$

representing the three-dimensional volume of an ellipse. Animals were sacrificed when their tumors reached 2 cm. Survival was evaluated from the first day of treatment until death. Tumor growth was evaluated from first day of treatment until day of first sacrifice (day 9).

Statistical Analysis

Statistical significance of differences observed in drug-treated versus control cultures was determined using Student's t test. The minimal level of significance was $p<0.05$. Analysis of synergism and antagonism with Compound (III) and dexamethasone was carried out using Median Dose Effect analysis in conjunction with the commercially-available software program Calcusyn (Biosoft, Ferguson, Mo., USA). The survival curves for mice were computed using the Kaplan-Meier method. The survival time differences between the control and treated group were compared using a log-rank test. The median survival times were compared using the Fisher-exact test. To compare the rate of tumor growth in the two arms, a linear mixed effect model (random coefficient model) was fitted.

Furthermore, the Examples demonstrate that Compound (III) inhibits myeloma cell growth at a median inhibitory concentration of less than 10 nM at 48 hours in MM cell lines resistant to conventional therapies, as well as MM patient cells, as determined by MTS assay and tritiated-thymidine uptake. MM.1S myeloma cell proliferation was also inhibited when co-cultured with bone marrow stromal cells, demonstrating ability to overcome the stimulatory effects of the bone marrow microenvironment. Pro-apoptotic effects were confirmed by Western blot. Significant cleavage of caspase 8, caspase 9, caspase 3 and PARP were observed with 20 nM of Compound (III) in MM.1S cells, indicating involvement of both the intrinsic and extrinsic apoptotic pathways in Compound (III)-mediated apoptosis. There was associated up-regulation of p21 and down-regulation of c-myc. Synergistic activity was observed in combination with proteasome inhibitor bortezomib. Compound (III)-induced HDAC inhibition resulted in histone hyperacetylation at low nanomolar concentrations. Acetylation of α-tubulin is a post-translational modification that consists of the addition of an acetyl group to lysine 40, which is reversed by HDAC6, or tubulin deacetylase (TDAC). Tubulin acetylation plays an important role in the differentiation of microtubule structure and function. Furthermore, TDAC constitutively binds both polyubiquitinated misfolded proteins and dynein, recruiting misfolded protein to dynein motors for transport to aggresomes along microtubules, which serves an important defense mechanism against apoptosis in MM cells. Importantly, dose-dependent inhibition of TDAC in MM.1S cells was observed at low nanomolar concentrations of Compound (III).

It is one objective of this invention to provide a pharmaceutical composition comprising a quantity, which is jointly therapeutically effective against myeloma comprising the COMBINATION OF THE INVENTION. In this composition, the combination partners can be administered together, one after the other or separately in one combined unit dosage form or in two separate unit dosage forms. The unit dosage form may also be a fixed combination.

The pharmaceutical compositions for separate administration of the combination partners and for the administration in a fixed combination, i.e., a single galenical composition comprising at least two combination partners, according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application.

Novel pharmaceutical composition contain, e.g., from about 10% to about 100%, preferably from about 20% to about 60%, of the active ingredients. Pharmaceutical preparations for the combination therapy for enteral or parenteral administration are, e.g., those in unit dosage forms, such as sugar-coated tablets, tablets, capsules or suppositories, and furthermore ampoules. If not indicated otherwise, these are prepared in a manner known per se, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partner of the COMBINATION OF THE INVENTION may be administered simultaneously or sequentially and in any order, and the components may be administered separately or as a fixed combination. For example, the method of treatment of myeloma according to the present invention may comprise:
  (i) administration of a combination partner (a) in free or pharmaceutically acceptable salt form; and
  (ii) administration of a combination partner (b) in free or pharmaceutically acceptable salt form, simultaneously or sequentially in any order, in jointly therapeutically effective amounts, preferably in synergistically effective amounts, e.g., in daily dosages corresponding to the amounts described herein.

The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of the compounds used for inhibiting the HDAC activity and of the combination partners employed in the COMBINATION OF THE INVENTION may vary depending on the particular compound or pharmaceutical composition employed, the mode of administration, the type of the myeloma being treated, the severity of the myeloma being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of compounds inhibiting the HDAC activity or of the single active ingredients of the COMBINATION OF THE INVENTION required to prevent, counter or arrest the progress of the condition. Optimal precision in achieving concentration of the active ingredients within the range that yields efficacy without toxicity requires a regimen based on the kinetics of the active ingredients' availability to target sites.

Moreover, the present invention provides a commercial package comprising as active ingredients the COMBINATION OF THE INVENTION, together with instructions for simultaneous, separate or sequential use thereof in the treatment of myeloma.

The present invention also provides the use of a compound of formula (I), as defined herein, and the use of a COMBINATION OF THE INVENTION for the preparation of a medicament for the treatment of myeloma.

What is claimed:

1. A method of treating multiple myeloma in a human patient in need thereof comprising administering in an amount which is synergistically effective, a combination of N-hydroxy-3-[4-[[[2-(2-methyl-1H-indol3-yl)-ethyl]-amino]methyl]phenyl]-2E-2-propenamide having the formula (III)

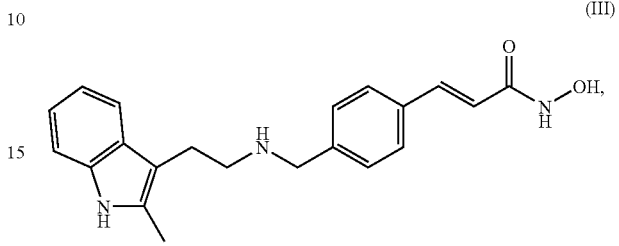

or a pharmaceutically acceptable salt thereof and bortezomib or a pharmaceutically acceptable salt thereof, wherein the multiple myeloma is resistant to conventional therapy.

2. The method of claim 1, wherein the multiple myeloma is resistant to bortezomib.

* * * * *